US009017299B2

(12) United States Patent
Iwase et al.

(10) Patent No.: US 9,017,299 B2
(45) Date of Patent: Apr. 28, 2015

(54) MEDICAL HOLLOW NEEDLE AND METHOD FOR PRODUCING THE SAME

(75) Inventors: Yoshiharu Iwase, Osaka (JP); Yutaka Eizumi, Osaka (JP)

(73) Assignee: Nipro Corporation, Osaka-shi (JP)

( * ) Notice: Subject to any disclaimer, the term of this patent is extended or adjusted under 35 U.S.C. 154(b) by 49 days.

(21) Appl. No.: 13/881,913

(22) PCT Filed: Nov. 29, 2011

(86) PCT No.: PCT/JP2011/077501
§ 371 (c)(1),
(2), (4) Date: Apr. 26, 2013

(87) PCT Pub. No.: WO2012/073947
PCT Pub. Date: Jun. 7, 2012

(65) Prior Publication Data
US 2013/0218102 A1    Aug. 22, 2013

(30) Foreign Application Priority Data

Nov. 29, 2010    (JP) ................................. 2010-265769

(51) Int. Cl.
*A61M 5/32* (2006.01)
*A61M 5/00* (2006.01)
(Continued)

(52) U.S. Cl.
CPC .................. *A61M 5/00* (2013.01); *A61M 5/158* (2013.01); *A61M 5/3286* (2013.01); *A61M 5/42* (2013.01); *B24B 19/16* (2013.01)

(58) Field of Classification Search
CPC .................................................. A61M 5/3268

USPC ........................................... 604/272, 239, 274
See application file for complete search history.

(56) References Cited

U.S. PATENT DOCUMENTS

| 5,752,942 A | 5/1998 | Doyle et al. |
| 6,009,933 A | 1/2000 | Doyle et al. |

(Continued)

FOREIGN PATENT DOCUMENTS

| CN | 1169320 | 1/1998 |
| DE | 10 2005 027 147 A1 | 12/2006 |

(Continued)

OTHER PUBLICATIONS

Jan. 17, 2012 International Search Report issued in International Application No. PCT/JP2011/077501 (with translation).

(Continued)

*Primary Examiner* — Nicholas Lucchesi
*Assistant Examiner* — Melissa A Snyder
(74) *Attorney, Agent, or Firm* — Oliff PLC

(57) ABSTRACT

A medical hollow needle structured in accordance with the present invention, wherein the puncture resistance of a blade surface over the entire length in the puncture direction can be made substantially equal, and the patient's pain during needle puncture can be relieved due to a reduction in the peak level of puncture pain with the duration of sensory awareness of the puncture pain shortened by the use of the blade surface in a novel shape employing, in combination with each other, first to fourth inclined surfaces having specific inclination directions. Accordingly, the present invention provides a medical hollow needle with a blade surface in a novel shape whereby the puncture pain can be further reduced compared to needles with a conventional structure, and to provide a preferred method of producing such a medical hollow needle.

8 Claims, 11 Drawing Sheets

(51) Int. Cl.
*A61M 5/158* (2006.01)
*A61M 5/42* (2006.01)
*B24B 19/16* (2006.01)

(56) References Cited

U.S. PATENT DOCUMENTS 6,517,523 B1   2/2003   Kaneko et al.
2001/0039402 A1*  11/2001   Prais et al. .................. 604/239

FOREIGN PATENT DOCUMENTS

FR          1225009 A    6/1960
JP          A-10-57490   3/1998
JP          A-2000-262615  9/2000

OTHER PUBLICATIONS

International Preliminary Report on Patentability issued in International Application No. PCT/JP2011/077501 on Jun. 4, 2013 (with translation).

Jul. 25, 2014 Office Action issued in Chinese Patent Application No. 201180057355.9 (with English translation).

Nov. 11, 2014 Office Action issued in Japanese Patent Application No. 2010-265769.

* cited by examiner

PUNCTURE RESISTANCE (COMPARATIVE EXAMPLE 1)

PUNCTURE RESISTANCE (COMPARATIVE EXAMPLE 2)

MEDICAL HOLLOW NEEDLE AND METHOD FOR PRODUCING THE SAME

TECHNICAL FIELD

The present invention relates to a medical hollow needle used for the subcutaneous injection, dialysis, drip infusion, blood collection, blood transfusion, liquid transfusion and the like, and to a method for producing the same.

BACKGROUND ART

Conventionally, medical hollow needles such as injection needles have been used in injecting drug solution, blood or the like into the body, or in collecting blood and other fluids therefrom. Such a medical hollow needle is made in a sharp shape with a beveled blade surface formed at the tip of a thin cylindrical needle tube.

There are various ways of forming the blade surface, one of which is a cutting method called "lancet cut." The lancet cut is provided with a first inclined surface on the base side, whereas, a second inclined surface and a third inclined surface are provided on either side of the circumference toward the tip of the blade surface, inclined at the same angle in the direction opposite to each other around the central axis, while having an inclination angle larger than that of the first inclined surface.

Meanwhile, in using such a medical hollow needle, it is important to relieve the patient's pain at the time of inserting the needle, and for that purpose, a reduction in puncture resistance is required.

In order to meet such a requirement, Unexamined Japanese Patent Publication No. JP-A-10-57490 (Patent Document 1) and Unexamined Japanese Patent Publication No. JP-A-2000-262615 (Patent Document 2) propose a shape of a blade surface wherein a fourth inclined surface and fifth inclined surface are provided between the first and second inclined surfaces and between the first and third inclined surfaces, respectively. The fourth inclined surface located between the first and second inclined surfaces has a smaller rotational angle (angle in the circumferential direction) than that of the second inclined surface around the central axis relative to the first inclined surface, and at the same time, has an inclination angle against the central axis larger than the first inclined surface and smaller than the second inclined surface. Also, the fifth inclined surface located between the first and third inclined surfaces has a smaller rotational angle (angle in the circumferential direction) than that of the third inclined surface around the central axis relative to the first inclined surface, and at the same time, has an inclination angle against the central axis larger than the first inclined surface and smaller than the third inclined surface.

However, upon examination by the inventors, it became clear that the medical hollow needle in a shape of a blade surface with the first to fifth inclined surfaces described in Patent Documents 1 and 2 still has a room to improve the effect of reducing puncture resistance. Especially in the medical hollow needle with a conventional structure, as shown in FIG. 3 of Patent Document 1, puncture resistance gradually increases during the needle puncture all the way from the tip end (blade edge portion) to the base end (heel portion) via the intermediate portion (ridge), and at the same time, puncture resistance gets too large at the base end as compared to the tip end and intermediate portion. For that reason, the puncture pain was continuously felt, and there was a risk of feeling a significant puncture pain at the end.

BACKGROUND ART DOCUMENTS

Patent Documents

Patent Document 1: JP-A-10-57490
Patent Document 2: JP-A-2000-262615

SUMMARY OF THE INVENTION

Problem the Invention Attempts to Solve

The present invention was made against the background described above, and the problem to be solved thereby is to provide a medical hollow needle with a blade surface in a novel shape whereby the puncture pain can be further reduced compared to needles with a conventional structure, and to provide a preferred method of producing such a medical hollow needle.

Means for Solving the Problem

A first mode of the present invention according to a medical hollow needle including a needle tube in a cylindrical shape with a blade surface inclined against a central axis thereof at a tip of the needle tube, characterized in that: the blade surface comprises: (i) a first inclined surface located on a base end side; (ii) a second inclined surface and a third inclined surface, which are located on a tip end side and provided with a same rotational angle in a direction opposite to each other around the central axis relative to the first inclined surface, and with a same inclination angle to the central axis, while being larger than that of the first inclined surface; and (iii) fourth inclined surfaces located between the first and second inclined surfaces and between the first and third inclined surfaces with rotational angles around the central axis which are same as that of the first inclined surface, and with inclination angles to the central axis larger than that of the first inclined surface, while being smaller than that of the second and third inclined surfaces.

In the medical hollow needle structured in accordance with the first mode, the ridges between the first inclined surface located on the base end side of the blade surface and the second and third inclined surfaces located on the tip end side of the blade surface is each removed in a beveled manner by the fourth inclined surface. This suppresses the peak value of the resistance when such ridges were to be inserted, thus relieving the puncture pain.

Especially in the present mode, the second and third inclined surfaces are each provided by rotating in the direction opposite to each other around the central axis relative to the first inclined surface, whereas the fourth inclined surface is not made as one to be provided by rotating around the central axis relative to the first inclined surface. Thus, by newly adopting the fourth inclined surfaces with the same rotational angle around the central axis as that of the first inclined surface and placing them between the first and second inclined surfaces and between the first and third inclined surfaces, it was made possible to substantially equalize puncture resistance of the blade surface over the entire length in the puncture direction from the tip end to the base end via the intermediate portion. As a result, the peak level of puncture resistance can be suppressed especially in the intermediate portion between the tip end (blade edge portion) and the base end (heel portion) as compared to the medical hollow needle with a conventional structure wherein puncture resistance gradually increases over the entire blade surface.

In the present invention, the second to sixth modes described below are more preferably adopted in proper combination with the first mode, thereby further improving the effect of reducing puncture resistance.

In other words, a second mode of the present invention is the medical hollow needle according to the first mode, wherein the inclination angle of the first inclined surface relative to the central axis is set at 10±2 degrees, the inclination angles of the second and third inclined surfaces relative to the central axis are both set at 18±2 degrees, and the inclination angle of the fourth inclined surface relative to the central axis is set at 12±2 degrees.

Also, a third mode of the present invention is the medical hollow needle according to the first or second mode, wherein an end of the fourth inclined surface on a side of the first inclined surface is located on the base end side from a center in a central axis direction of the blade surface, while an end of the fourth inclined surface on a side of the second and third inclined surfaces is located on the tip end side from the center in the central axis direction of the blade surface.

Furthermore, a fourth mode of the present invention is the medical hollow needle according to any one of the first to third modes, wherein ends of the second and third inclined surfaces on the base end side are located at ¼ to ¾ of a length from the tip end to the base end of the blade surface in the central axis direction.

Also, a fifth mode of the present invention is the medical hollow needle according to any one of the first to fourth modes, wherein a fifth inclined surface is provided at the ridge created by the second and third inclined surfaces at the tip end of the blade surface with the rotational angle set at the same as that of the first inclined surface around the central axis.

As to the medical hollow needle according to the fifth mode, it is more preferable to provide the fifth inclined surface as an extension of the fourth inclined surface.

Meanwhile, what the present invention according to a method of producing a medical hollow needle is characterized by is a method of producing a medical hollow needle that forms a blade surface inclined against a central axis of a needle tube by means of processing a tip of the needle tube of a cylindrical shape with a grinding tool, the method comprising: (I) a step of forming a first inclined surface located on a base end side of the blade surface by grinding with a first processing surface inclined against the central axis; (II) a step of forming a second inclined surface located on one side in a circumferential direction at a tip end side of the blade surface by grinding with a second processing surface having an inclination angle larger than that of the first inclined surface relative to the central axis by means of differentiating a relative position between the needle tube and the grinding tool by a given rotational angle in one direction around the central axis in reference to the relative position between the grinding tool that grinds the first inclined surface and the needle tube; (III) a step of forming a third inclined surface located on another side in the circumferential direction at the tip end side of the blade surface by grinding with a third processing surface having a same inclination angle as that of the second inclined surface against the central axis by means of differentiating the relative position between the needle tube and the grinding tool by a same rotational angle as that of the second inclined surface in an opposite direction thereof around the central axis in reference to the relative position between the grinding tool that grinds the first inclined surface and the needle tube; and (IV) a step of forming fourth inclined surfaces with a same rotational angle as that of the first inclined surface each located between the first and second inclined surfaces and between the first and third inclined surfaces by grinding with a fourth processing surface having an inclination angle larger than that of the first inclined surface but smaller than that of the second and third inclined surfaces against the central axis at the relative position between the grinding tool that grinds the first inclined surface and the needle tube.

According to the method of the present invention, a blade surface with first to fourth inclined surfaces can be formed at the tip end of the needle tube by applying multiple grinding processes by means of rotating the needle tube for positioning relative to the grinding tool by a given angle around the central axis of the needle tube, thus enabling to efficiently produce a medical hollow needle with the structure according to the present invention described.

Also, in the present method of invention, the implementation order of each grinding process with the first to fourth processing surfaces is not limited, but the fourth inclined surface can be formed after forming each of the first, second and third inclined surfaces, for example.

Effect of the Invention

The medical hollow needle provided with the structure according to the present invention makes it possible to substantially equalize puncture resistance of the blade surface over the entire length in the puncture direction to achieve a reduction in the peak level of puncture resistance, thus relieving the patient's pain during needle puncture by the use of the blade surface in a novel shape employing, in combination with each other, first to fourth inclined surfaces having specific inclination directions.

Also, according to the present method of invention, it is possible to efficiently produce a medical hollow needle with the structure according to the present invention with a blade surface in a novel shape provided with first to fourth inclined surfaces by applying multiple grinding processes while changing the position of the grinding tool relative to the needle tube.

EMBODIMENTS FOR CARRYING OUT THE INVENTION

Figure 1:
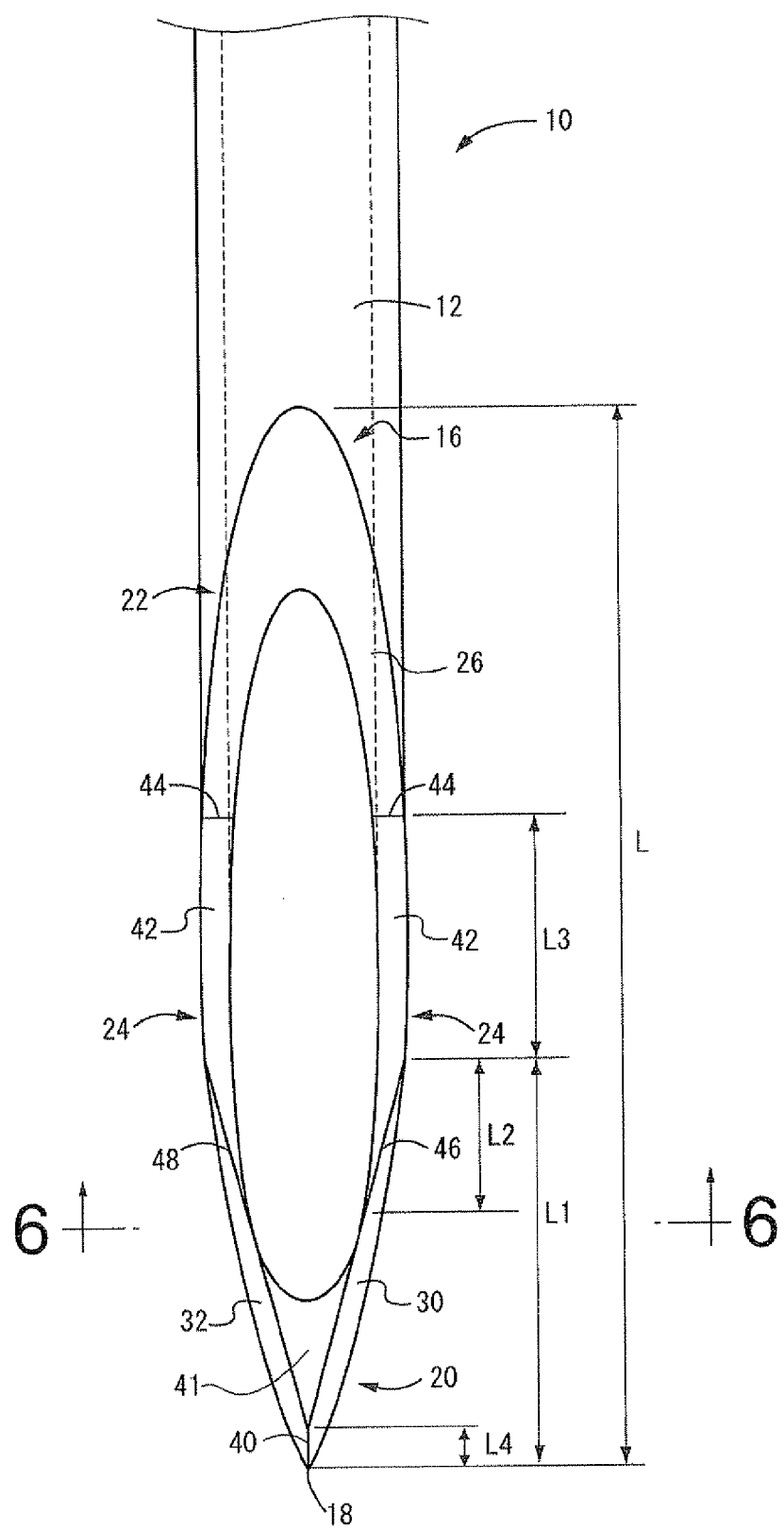
[FIG. 1] A plan view showing a medical hollow needle as an embodiment of the present invention.

Embodiments of the present invention will be described below in reference to the drawings. FIGS. 1 to 6 show a medical hollow needle 10 as one embodiment of the present invention. The medical hollow needle 10 is provided with a blade surface 16 inclined against a central axis 14 of a needle tube 12 (see FIGS. 2 and 3) at the tip end thereof.

More specifically, the needle tube 12 shown in the drawings as an embodiment has a shape of a linear tube extending straight with a circular cross-section. However, as such needle tube 12, proper sizes and shapes can be adopted depending on the intended use of the medical hollow needle 10, and a tapered tube shape can be adopted, for example, wherein a tapered portion that gradually changes its diameter along the central axis either toward the tip side or the base side is formed for the entire length or partially formed in the central axis direction. Also, the tapered portion can be provided so as to gradually vary its diameter from a middle position in the axial direction of the blade surface 16 toward the central axis. Furthermore, the needle tube 12 can be made in a curved shape for the entire length or partially in the central axis direction.

Meanwhile, the blade surface 16 formed on the tip side of the needle tube 12 comprises a tip end portion (blade edge portion) 20 including a blade tip 18, a base end portion (heel portion) 22 located at the opposite end from the blade tip 18, and an intermediate portion 24 located in the middle of these tip end portion 20 and base end portion 22. The phrase "left and right" in the following descriptions means the left and right in FIG. 1 (also in FIGS. 5 and 6). That is, the blade surface 16 is closed along the circumferential direction with continuous left and right sides at the tip end portion 20 and the base end portion 22, while being separated in the intermediate portion 24.

Then, the tip end portion 20, base end portion 22, and intermediate portion 24 that together comprise the blade surface 16 are provided with inclined surfaces different from each other.

Figure 5:
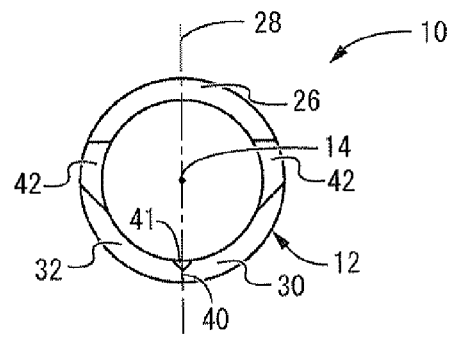
[FIG. 5] A front view of the medical hollow needle shown in FIG. 1.
Figure 6:
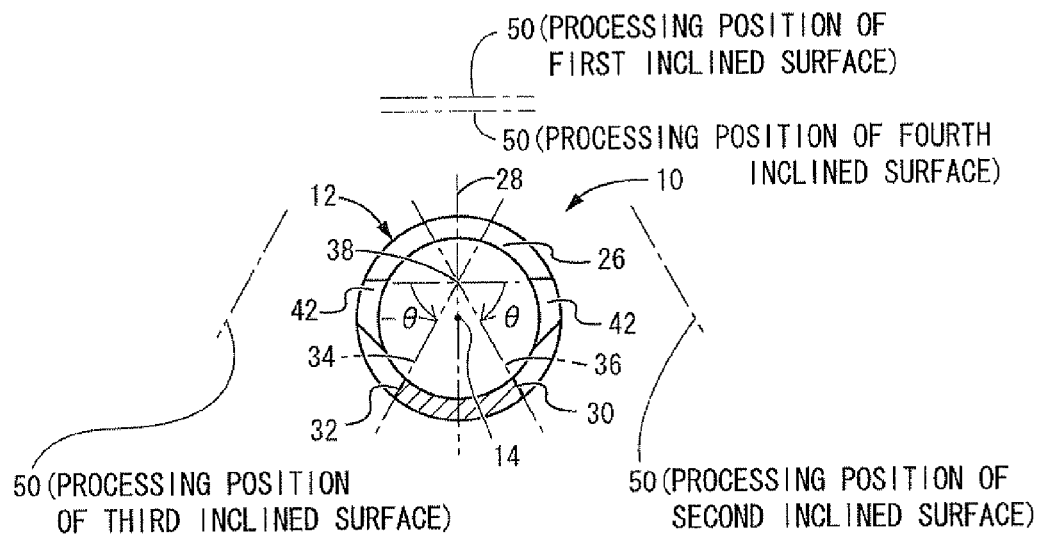
[FIG. 6] A cross-section 6-6 of FIG. 1.

First, the base end portion 22 of the blade surface 16 is provided with a first inclined surface 26 inclined in the axial direction by a given angle α against the central axis 14. The entire blade surface 16 is made plane symmetrical to a plane 28 that includes the central axis 14 as shown in FIGS. 5 and 6.

Also, the tip end portion 20 of the blade surface 16 is provided with a second inclined surface 30 extending from the blade tip 18 to one side in the circumferential direction (to the right) and a third inclined surface 32 extending from the blade tip 18 to the other side (to the left) in the circumferential direction. The second inclined surface 30 and third inclined surface 32 have rotational angles θ and −θ that are rotated by equal angles in the opposite directions around the central axis 14 relative to the first inclined surface 26. In other words, extended lines 34 and 36 of the second inclined surface 30 and third inclined surface 32, respectively, intersect each other as shown in FIG. 6 at a central angle (180 degree—2θ) at an intersection 38 located on the plane 28 that serves as a bisector passing through the blade tip 18.

Figure 2:
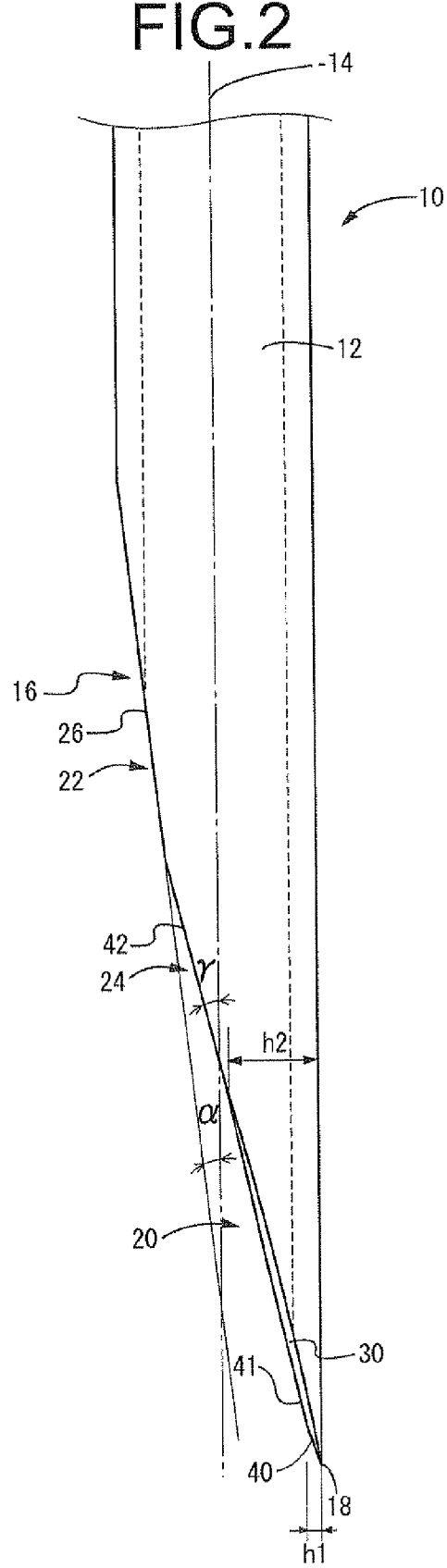
[FIG. 2] A side view of the medical hollow needle shown in FIG. 1.
Figure 3:
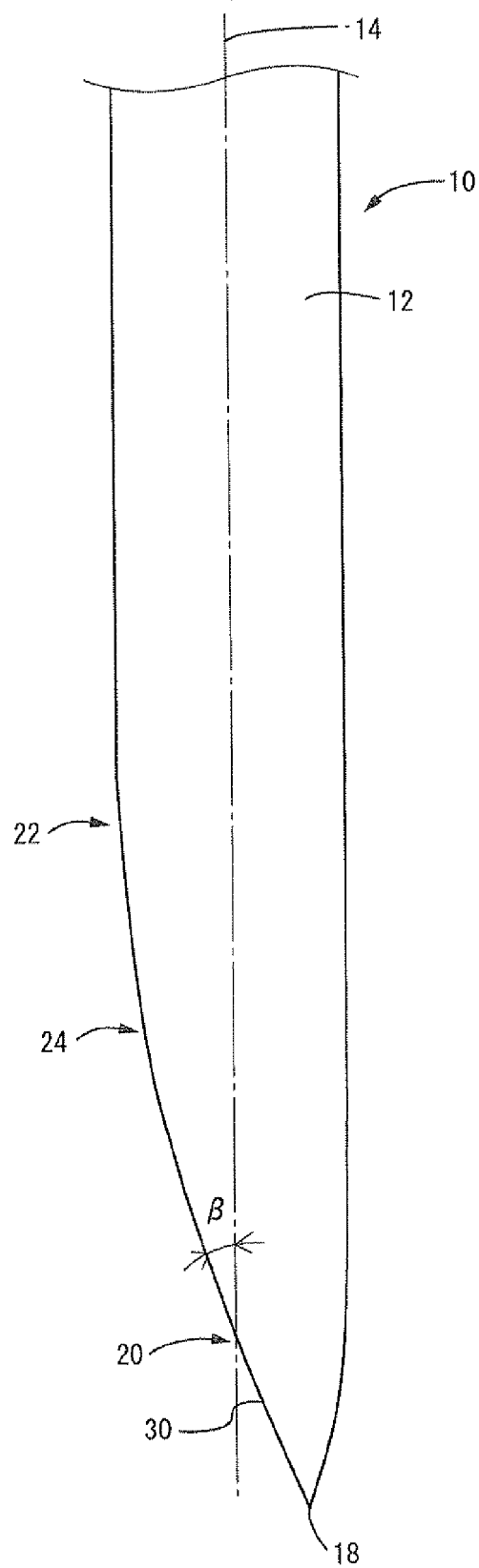
[FIG. 3] A side view of the medical hollow needle shown in FIG. 2 rotated around the central axis by an angle (−θ) in the circumferential direction of a second inclined surface.
Figure 4:
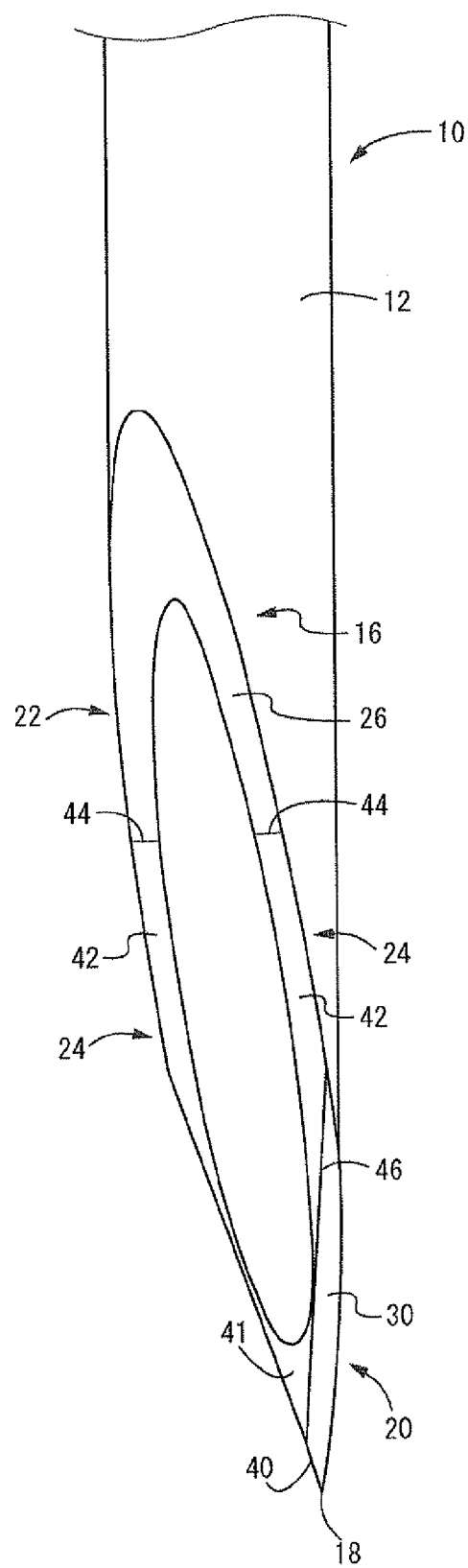
[FIG. 4] An axonometric view of a blade surface of the medical hollow needle shown in FIG. 1.

Furthermore, the second inclined surface 30 and third inclined surface 32 are inclined at the same angle to the central axis 14 in the axial direction, too. The inclination angle β of the second inclined surface 30 and third inclined surface 32 in the axial direction is an angle at which each of the inclined surfaces 30 and 32 intersects with the central axis 14. In other words, the intersecting angle between the second inclined surface 30 and the central axis 14 turns out to be the inclination angle β of the second inclined surface 30 in the side view parallel to the second inclined surface 30 in which the second inclined surface 30 appears as a straight line as shown in FIG. 3 after rotating the side view in which the first inclined surface 26 appears as a straight line as shown in FIG. 2 by a rotational angle of −θ. The inclination angle β of the third inclined surface 32 in the axial direction can also be understood as an intersecting angle between the third inclined surface 32 and the central axis 14 in the side view rotated by an angle θ around the central axis 14 from the side view shown in FIG. 2.

In the present embodiment, a blade edge ridge 40 is formed extending with an inclination against the central axis 14 in a straight line at the junction of the second inclined surface 30 and third inclined surface 32 of the tip end portion 20. The tip end of this blade edge ridge 40 reaches the blade tip 18 made in a sharp shape, while a central tip inclined surface 41 is formed to extend in the area between the second inclined surface 30 and third inclined surface 32 on the back end side of the blade edge ridge 40. The central tip inclined surface 41 is formed in such a way that it cuts away the back end apex of the blade edge ridge 40, which is the intersection of the second inclined surface 30, third inclined surface 32 and the inner surface of the needle tube 12, and especially in the present embodiment, the central tip inclined surface 41 is made in the same plane as the fourth inclined surface 42 described later (an extension of the fourth inclined surface 42).

Moreover, in the intermediate portion 24 of the blade surface 16, fourth inclined surfaces 42, 42 are provided separately on the left and right sides both inclined against the central axis 14 by a given angle γ in the axial direction. The fourth inclined surface 42 is made to incline in the same direction as the first inclined surface 26 against the central axis 14 and to incline in the axial direction by a different angle from that of the first inclined surface 26. In other words, the rotational angle of the fourth inclined surface 42 around the central axis 14 is made equal to that of the first inclined surface 26. Then, the inclination angle γ of the fourth inclined surface 42 in the axial direction is made larger than the inclination angle α of the first inclined surface 26 in the axial direction and smaller than the inclination angle β of the second inclined surface 30 and third inclined surface 32 in the axial direction as indicated by the following formula:

$$\alpha < \gamma < \beta$$

Also, the fourth inclined surface 42 is provided at the borders between the first inclined surface 26 and second inclined surface 30 and between the first inclined surface 26 and third inclined surface 32 so as not to have the first inclined surface 26 get in contact with the second inclined surface 30 or third inclined surface 32 on either side of the intermediate portion 24 of the blade surface 16. In other words, the fourth inclined surface 42 is interposed between the first inclined surface 26 and second inclined surface 30 as well as between the first inclined surface 26 and third inclined surface 32 for the entire area of the borders. And the first inclined surface 26 makes contact only with the fourth inclined surface 42 on the blade surface 16 without contacting either the second inclined surface 30 or third inclined surface 32.

Then, first ridge lines 44 and 44 that mark the border between the first inclined surface 26 and the fourth inclined surfaces 42, 42 extend to be separated in the left and right directions respectively as shown in the plan view of FIG. 1.

Meanwhile, a second ridge line 46 that marks the border between the second inclined surface 30 and fourth inclined surface 42 as well as a third ridge line 48 that marks the border between the third inclined surface 32 and fourth inclined surface 42 extend in a straight line, as shown in the plan view of FIG. 1, inclined in the direction of gradually opening up from the inner to outer circumference of the blade surface 16 as they move from the tip end portion 20 to the base end portion 22.

Thus, using the blade surface 16 comprising the first inclined surface 26, second inclined surface 30, third inclined surface 32, fourth inclined surfaces 42, 42, and the central tip inclined surface 41 as a fifth inclined surface, it is not only possible to suppress the peak level of puncture resistance generated each time the tip end portion 20, the intermediate portion 24, and the base end portion 22 are punctured and inserted in this sequence, but it is also possible to reduce the difference of puncture resistance values between them. As a result, the level of the patient's pain at the time of puncture using the medical hollow needle 10 is reduced with the duration of sensory awareness of the puncture pain shortened, thus relieving the patient's suffering.

The achievability of the above effects are obvious from the measurement results in Example described later, but it seems to bear a significant meaning that the rotational angles of the fourth inclined surfaces 42, 42 interposed between the first inclined surface 26 and second inclined surface 30 and between the first inclined surface 26 and third inclined surface 32 were each made to be the same as that of the first inclined surface 26, while the inclination angles of the fourth inclined surfaces 42, 42 in the axial direction were each made larger than that of the first inclined surface 26 and smaller than that of the second inclined surface 30 or third inclined surface 32, in addition to the fact that the second inclined surface 30 and third inclined surface 32 were each given an inclination angle in the axial direction together with a rotational angle (inclination angle in the circumferential direction).

In other words, by configuring the tip end portion 20 of the blade surface 16 with the second inclined surface 30 and third inclined surface 32 at rotational angles $\theta$ and $-\theta$ in addition to the large inclination angle $\beta$ in the axial direction, reductions in the peak level of puncture resistance and the puncture pain can be expected. Also, especially in the present embodiment, further reductions in puncture resistance at the tip end portion 20 and the puncture pain can be achieved by lowering the height of the blade edge ridge 40 (h1 in FIG. 2) by means of forming the central tip inclined surface 41 at the tip end portion 20. Then, in the next intermediate portion 24, a variation in puncture resistance as the puncture position moves from the second inclined surface 30 and third inclined surface 32 of the tip end portion 20 to the fourth inclined surface 42 of the intermediate portion 24 and a variation in puncture resistance as the puncture position moves from the fourth inclined surface 42 to the first inclined surface 26 of the base end portion 22 can both be suppressed by means of configuring the blade surface with the fourth inclined surface 42 at an inclination angle $\beta$ in the axial direction and the same rotational angle as that of the first inclined surface 26 of the base end portion 22.

The second inclined surface 30 and third inclined surface 32 of the tip end portion 20 only exert small puncture resistance by having the rotational angles $\theta$ and $-\theta$, whereas the fourth inclined surface 42 suppresses puncture resistance by having the inclination angle $\gamma$ smaller than those of the second inclined surface 30 and third inclined surface 32 in the axial direction. In addition, because the fourth inclined surface 42 has no rotational angle (inclination angle in the circumferential direction), movements of the puncture position from the second inclined surface 30 and third inclined surface 32 to the fourth inclined surface 42 can be smoothly carried out without any drastic change in puncture resistance by providing the second ridge line 46 and third ridge line 48 that mark the borders between the second inclined surface 30 and the fourth inclined surface 42 and between the third inclined surface 32 and the fourth inclined surface 42 to extend in a long stretch while being inclined toward the central axis 14.

Moreover, since the fourth inclined surface 42 of the intermediate portion 24 has the same rotational angle as that of the first inclined surface 26 of the base end portion 22, any drastic change in puncture resistance can be suppressed even during the movement from the puncture position of the fourth inclined surface 42 to that of the first inclined surface 26. Therefore, it is now possible to perform a needle puncture without any drastic change in puncture resistance from the intermediate portion 24 to the base end portion 22 while suppressing the peak level of puncture resistance during needle puncture at the intermediate portion 24 and the base end portion 22 by means of properly setting the inclination angle $\gamma$ of the fourth inclined surface 42 in the axial direction and the inclination angle $\alpha$ of the first inclined surface 26 in the axial direction.

Additionally, since the fourth inclined surfaces 42, 42 are formed on both left and right sides in the intermediate portion in the axial direction of the blade surface 16, effects of "coring" can be prevented by inhibiting the incision of the target tissues such as skin by the blade surface 16 during needle puncture in patients. In other words, the effects of cutting the targeted tissues are caused by the outer peripheral edge, because the second inclined surface 30 and third inclined surface 32 are each given a rotational angle (inclination angle in the circumferential direction) during needle puncture at the time of inserting the tip end portion 20, but the angle heights of the second ridge line 46 and third ridge line 48 formed at the end of the second inclined surface 30 and third inclined surface 32 are lowered by the formation of the fourth inclined surfaces 42, 42 on the left and right sides in the intermediate portion in the axial direction of the blade surface 16, thus effectively suppress the incision (progression) into the target tissues.

At this point, a range of specific configurations of all parts of the blade surface 16 that can be preferably adopted is summarized below. By selecting values from this range, effects of lowered peak level of puncture resistance and reduction in the variation in puncture resistance at the time of needle puncture and so forth as described above can be obtained even more advantageously.

The angle $\alpha$ (inclination angle of the first inclined surface in the axial direction) is preferably set in a range of 8 to 12 degrees, and more preferably at 10±1 degrees. The angle $\beta$ (inclination angle of the second and third inclined surfaces in the axial direction) is preferably set in a range of 16 to 20 degrees, more preferably at 18±1 degrees. The angle $\gamma$ (inclination angle of the fourth inclined surface in the axial direction) is preferably set in a range of 10 to 14 degrees, more preferably at 12 ±1 degrees. The angle $\theta$ (rotational angle of the second and third inclined surfaces) is preferably set in a range that brings the value of the central angle 180—2$\theta$ equal to 100 to 120 degrees, more preferably to 110±5 degrees. L (entire length of the blade surface in the axial direction) is preferably set in a range of 3.6 to 4.0 mm, more preferably at 3.8±0.1 mm. L1 (length of the second or third inclined surface in the axial direction) is preferably set in a range of 1.3 to 1.7 mm, more preferably at 1.5±0.1 mm. L2 (length of the second or third ridge line in the axial direction) is preferably set in a range of 1.1 to 1.5 mm, more preferably at 1.3±0.1 mm. L3 (length of the fourth inclined surface in the axial direction) is preferably set in a range of 0.8 to 1.2 mm, more preferably at 1.0±0.1 mm. L4 (length of the blade edge ridge in the axial direction) is preferably set in a range of 0.12 to 0.16 mm, more preferably at 0.15 ±0.01 mm. I.D. (inner diameter of the needle tube) is preferably set in a range of 0.530 to 0.549 mm, more preferably at 0.5395±0.005 mm. O.D. (outer diameter of the needle tube) is preferably set in a range of 0.811 to 0.825 mm, more preferably at 0.818±0.005 mm.

Meanwhile, the medical hollow needle 10 with the structure described above is preferably produced in accordance with the following method:

First, the needle tube 12 as a raw tube produced from a proper material using a primary forming process is prepared. As materials of the needle tube 12, those that have been known to the public such as steel materials including stainless steel can be used. The length (L), inner diameter (I.D.) and outer diameter (O.D.) of the needle tube 12 are to be set as indicated above depending on the intended use of the medical hollow needle.

Next, by applying multiple grinding processes to the needle tube 12, which is a raw tube, the blade surface 16 having the first inclined surface 26, second inclined surface 30, third inclined surface 32, fourth inclined surfaces 42, 42 and central tip inclined surface 41 described above is formed.

More specifically, a grindstone in a disc (circular cylinder) shape with a given thickness is first used, being set up above the targeted first inclined surface 26 on the tip end side of the needle tube 12. Then, a rotation center axis 50 of the grindstone is set in the direction perpendicular to the symmetry plane 28 and parallel to the targeted first inclined surface 26 (see the processing position of the first inclined surface in FIG. 6) to form a first processing surface. The first processing surface of the grindstone thus arranged is rotationally driven around the rotation center axis 50 to perform a grinding/polishing (grinding/shaving) process on the tip end surface of the needle tube 12 over the entire surface in order to form the first inclined surface 26.

Next, by changing the relative position of the needle tube 12 and the grindstone to each other, the grinding process is repeated on the tip end surface of the needle tube 12. Due to the structure of the grinding device, it is preferable to fix the position of the grindstone and change the relative position of the needle tube 12.

In other words, the needle tube 12 and the grindstone are rotated relative to each other around the central axis of the needle tube 12 in the circumferential direction and then displaced relative to each other in the inclination direction against the central axis of the needle tube 12 to reset the relative position between the needle tube 12 and the grindstone before grinding the second inclined surface 30. More specifically, the second processing surface is formed by setting the rotation center axis 50 of the grindstone above the second inclined surface 30 and parallel thereto (see the processing position of the second inclined surface in FIG. 6). Then, the second inclined surface 30 is formed by means of rotationally driving the second processing surface of the grindstone around the rotation center axis 50 and grinding with its outer periphery the tip end portion 20 of the needle tube 12 on the right side starting from the blade tip 18.

Also, the third inclined surface 32 is ground after the relative position between the needle tube 12 and the grindstone is reset by rotating the needle tube 12 and the grindstone relative to each other around the central axis of the needle tube 12 in the circumferential direction. More specifically, the third processing surface is formed by setting the rotation center axis 50 of the grindstone above the targeted third inclined surface 32 and parallel thereto (see the processing position of the third inclined surface in FIG. 6). Then, the third inclined surface 32 is formed by means of rotationally driving the third processing surface of the grindstone around the rotation center axis 50 and grinding with its outer periphery the tip end portion 20 of the needle tube 12 on the left side starting from the blade tip 18.

Figure 7:
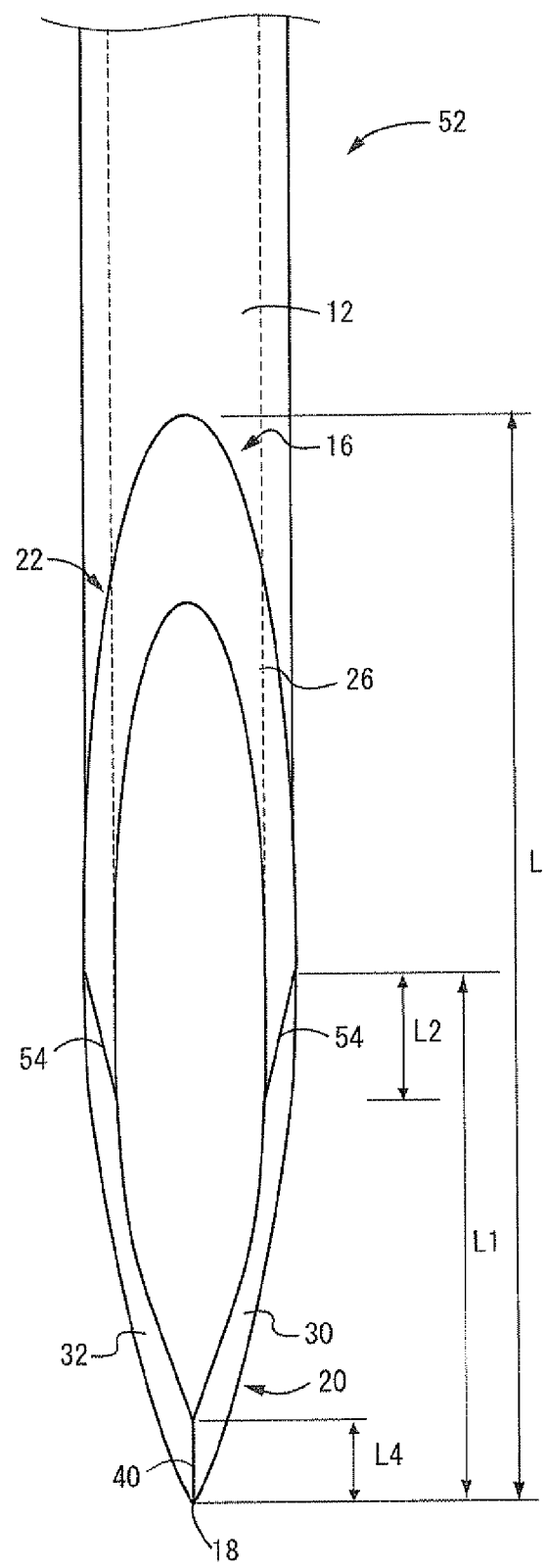
[FIG. 7] A plan view corresponding to FIG. 1 that shows an intermediate product of the medical hollow needle shown in FIG. 1.
Figure 8:
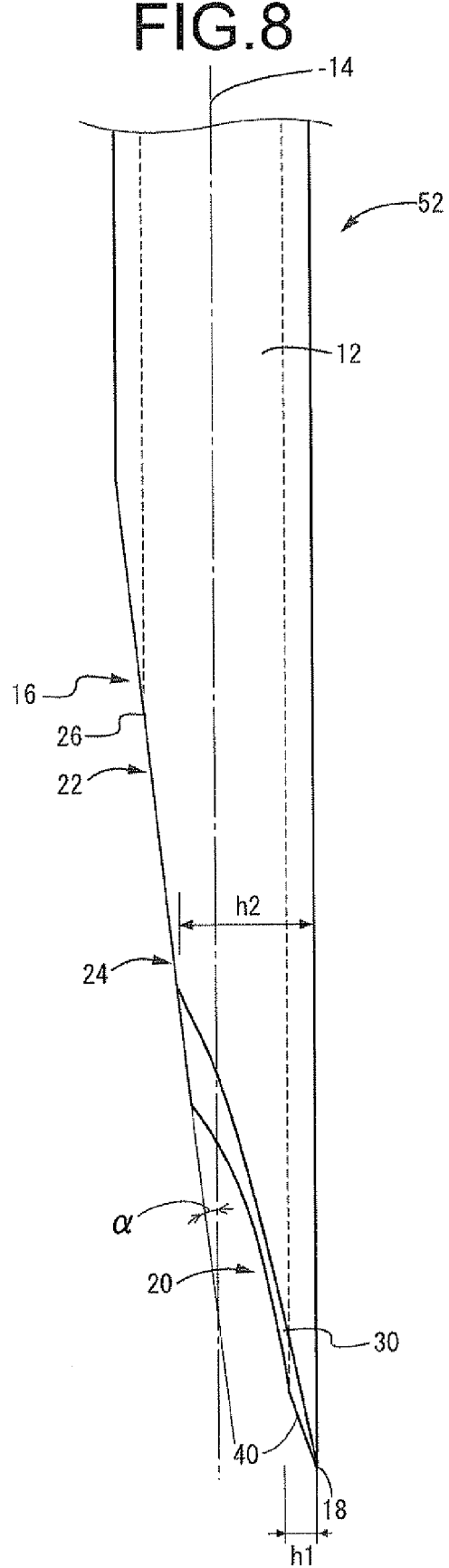
[FIG. 8] A side view corresponding to FIG. 2 that indicates the intermediate product of the medical hollow needle shown in FIG. 1.

Through the grinding processes described above, an intermediate product 52 like the one shown in FIGS. 7 and 8 is obtained. Subsequently, after a grinding process on the intermediate portion 24 of the blade surface 16 of the intermediate product 52, the fourth inclined surfaces 42, 42 are formed over ridges 54 in the intermediate portion 24 each existing at the border between the first inclined surface 26 and second inclined surface 30 and between the first inclined surface 26 and third inclined surface 32 so that such ridges 54 are eliminated.

For that purpose, the fourth processing surface is formed by placing the grindstone above the targeted fourth inclined surface 42 and setting the rotation center axis 50 of the grindstone in the direction perpendicular to the symmetry plane 28 and parallel to the targeted fourth inclined surface 42 (see the processing position of the fourth inclined surface in FIG. 6). By rotationally driving the fourth processing surface of the grindstone thus set up around the rotation center axis 50 and performing a grinding/polishing (grinding/shaving) process on the tip end surface of the needle tube 12 with the outer periphery of the grindstone, the fourth inclined surface 42 is formed. The fourth inclined surface 42 exists in a pair separate from each other on the left and right sides as shown in FIG. 6, and these fourth inclined surfaces 42, 42 can be formed simultaneously by a single grinding process. At the same time as the grinding process of such fourth inclined surfaces 42, 42, the central tip inclined surface 41 is formed by performing a grinding process in the area on the back end side of the blade edge ridge 40 at the tip end portion 20 using the same grinding processing surface.

The first inclined surface 26, second inclined surface 30, third inclined surface 32, fourth inclined surfaces 42, 42, and central tip inclined surface 41 are each made to be an exact or approximate flat surface. That is, each inclined surface can be made in an approximate flat surface if the outer diameter of the grindstone is set larger enough than that of the needle tube 12. Also, each of the inclined surfaces 26, 30, 32, 41, 42, 42 can be formed in a flat surface by means of shifting the rotation center axis 50 of the grindstone in parallel in the transaxial direction toward the position that corresponds to the inclination angles ($\alpha$, $\beta$, $\gamma$) in the axial direction of the inclined surfaces 26, 30, 32, 42, 42 to prepare for the cutting/shaving process.

Also, after forming the first inclined surface 26, second inclined surface 30, third inclined surface 32, fourth inclined surfaces 42, 42, and central tip inclined surface 41 by grinding/polishing (grinding/shaving) processes, it is desirable to apply a burr removal process using a blasting process and the like wherein glass beads of diameter about a few dozen microns ($\mu$) are blasted. During the blasting process, it is desirable to protect the blade tip 18 to maintain a sharp edge thereof. Also, it is desirable to remove burrs on the blade tip 18 separately by electrolytic treatments. After such a burr removal process, the medical hollow needle 10 undergoes anti-corrosion, cleaning and sterilization treatments.

The order of formation by the grinding process of the first inclined surface 26, second inclined surface 30, third inclined surface 32, fourth inclined surfaces 42, 42, and central tip inclined surface 41 is not limited to the one exemplified above. For example, after forming the first inclined surface 26, fourth inclined surfaces 42, 42, and central tip inclined surface 41, the second inclined surface 30 and third inclined surface 32 can be formed. Also, the fourth inclined surfaces 42, 42 and central tip inclined surface 41 can be formed by different grinding processes.

EXAMPLE

Figure 9:
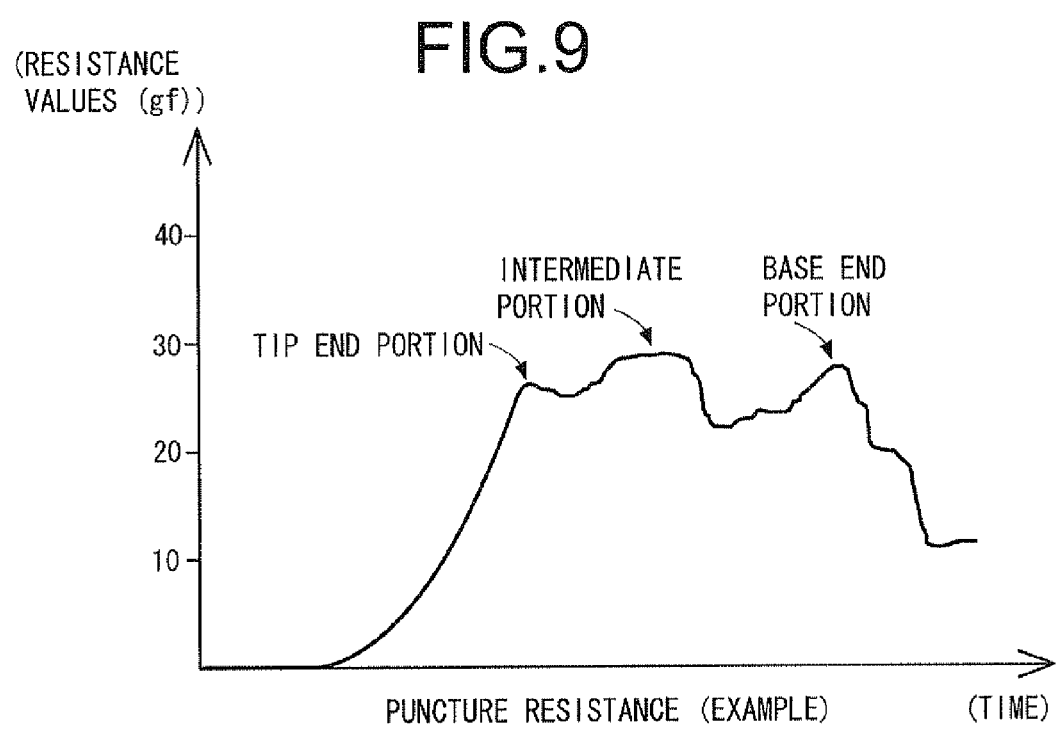
[FIG. 9] A graph showing measured values of puncture resistance of the medical hollow needle shown in FIG. 1.

FIG. 9 shows measurement results of puncture resistance of a medical hollow needle as Example having a structure shown in FIG. 1 to 6 as described above and the specific configuration shown in [Table 1] and [Table 2] below. Such measurements were taken by directing the central axis of the medical hollow needle toward the surface of a 0.04 mm urethane sheet and measuring resistance values (gf) as the needle advances at a constant speed of 20 mm/min to puncture and penetrate into the sheet. These measurement results reveal that the medical hollow needle structured in accordance with the present invention suppresses the peak value of puncture resistance at each puncture of the tip end portion 20, intermediate portion 24 and base end portion 22 at a low level without raising it higher, and the differences between the peak levels are kept small. In [Table 2], h2 indicates the height of the second and third ridge lines (see FIG. 2).

Figure 10:
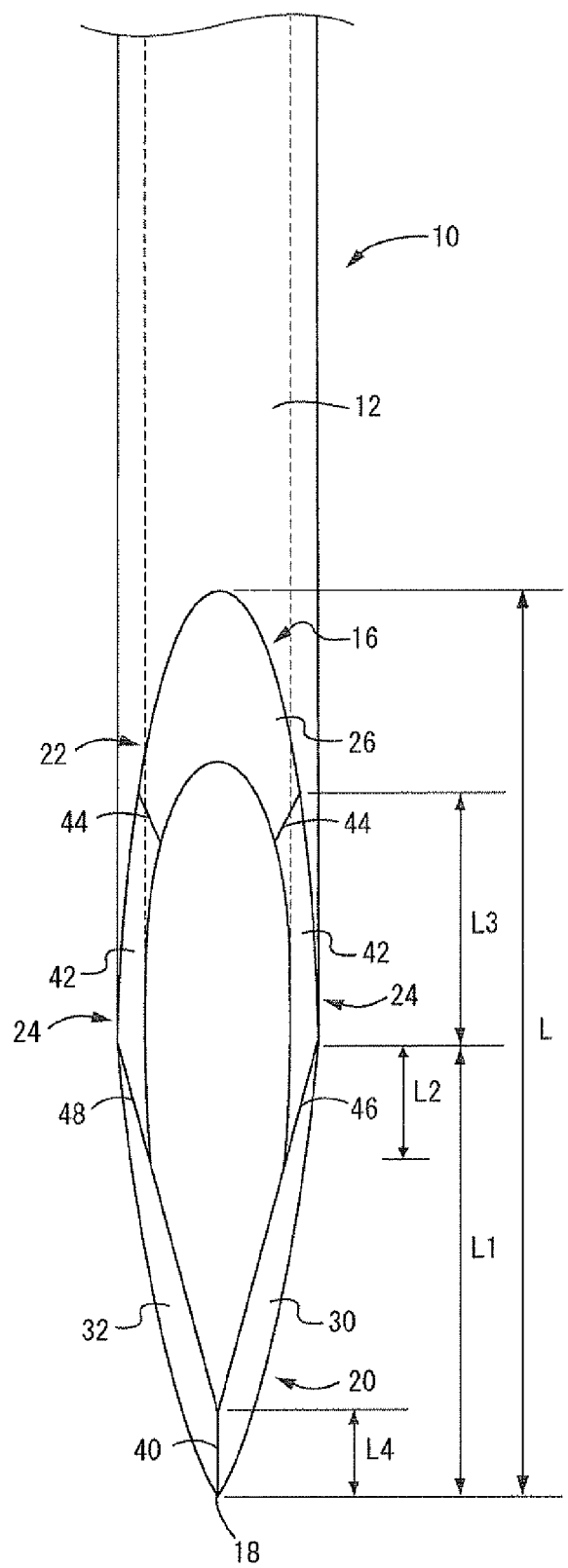
[FIG. 10] A plan view corresponding to FIG. 1 that shows a medical hollow needle as Comparative Example 2.
Figure 11:
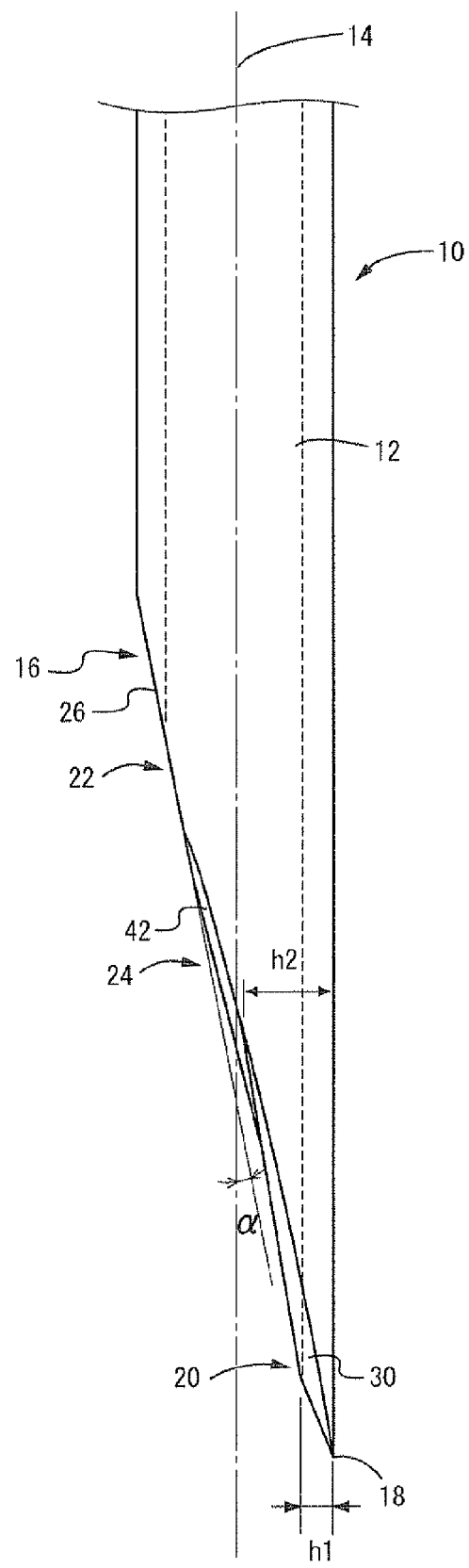
[FIG. 11] A side view of the medical hollow needle shown in FIG. 10 as Comparative Example 2.

Also, as Comparative Example 1, a medical hollow needle structured to provide none of the fourth inclined surfaces 42, 42 nor the central tip inclined surface 41 was prepared, while as Comparative Example 2, a medical hollow needle structured to have an inclination angle in the circumferential direction set for the fourth inclined surfaces 42, 42 in the same way as the second and third inclined surfaces was prepared. Then, for these medical hollow needles of Comparative Examples 1 and 2, measurements of puncture resistance were taken under the same conditions as those of Example of the present invention. Specific configurational dimensions of the medical hollow needles of Comparative Examples 1 and 2 are shown in the above [Table 1] and [Table 2] together with those of Example. Also, since the structure of the medical hollow needle of Comparative Example 1 is the same as that of the intermediate product shown in FIGS. 7 and 8, codes representing the part dimensions of Comparative Example 1 included in [Table 1] and [Table 2] are indicated in FIGS. 7 and 8. Meanwhile, as to the medical hollow needle of Comparative Example 2, its structure is shown in FIGS. 10 and 11, while the codes representing part dimensions of Comparative Example 2 included in [Table 1] and [Table 2] are indicated in FIGS. 10 and 11.

Figure 12:
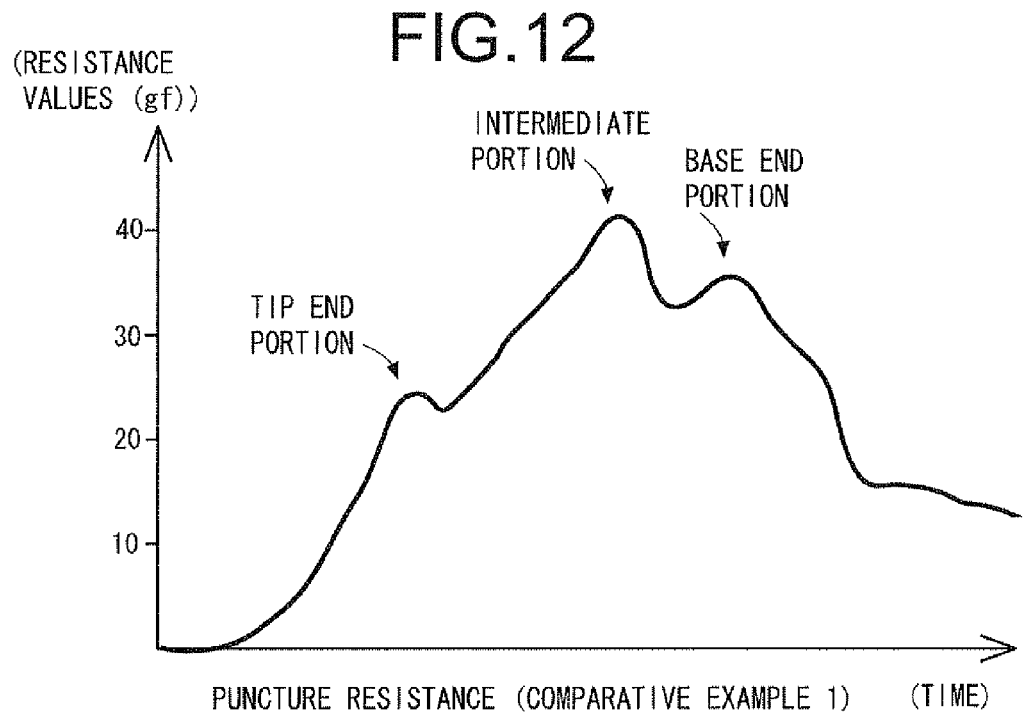
[FIG. 12] A graph showing measured values of puncture resistance of a medical hollow needle of Comparative Example 1.
Figure 13:
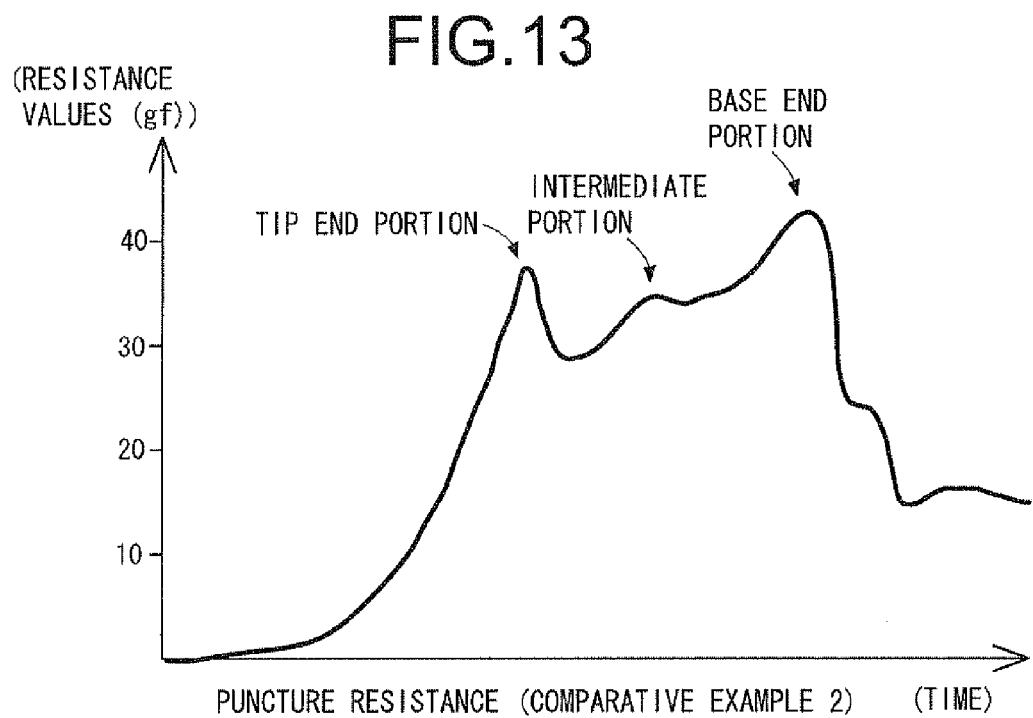
[FIG. 13] A graph showing measured values of puncture resistance of the medical hollow needle of Comparative Example 2.

As evident from FIGS. 12 and 13 that show measurement results of puncture resistance of Comparative Examples 1 and 2, respectively, these Comparative Examples 1 and 2 have larger differences among peak level of puncture resistance of the tip end portion 20, intermediate portion 24, and base end portion 22 as well as higher peak levels as compared to those of Example described above. This explains that the medical hollow needle of Example according to the present invention has smaller puncture resistance than conventional products and is able to relieve puncture pain.

KEYS TO SYMBOLS

10: Medical hollow needle; 12: Needle tube; 14: Central axis; 16: Blade surface; 26: First inclined surface; 30: Second inclined surface; 32: Third inclined surface; 41: Central tip inclined surface (fifth inclined surface); 42: Fourth inclined surface

TABLE 1

| Angle name | 10 ± 2 (Inclination angle of 1st inclined surface in axial direction) 1st bevel (deg.) | 18 ± 2 (Inclination angle of 2nd and 3rd inclined surfaces in axial direction) 2nd/3rd bevels (deg.) | | (Inclination angle of 4th inclined surface in axial direction) 4th bevel (deg.) | 110 ± 10 Central angle (180−2θ) | | 3.8 ± 0.2 Length of blade surface L (mm) |
|---|---|---|---|---|---|---|---|
| | | (left) | (right) | | 2nd & 3rd bevels (deg.) | 4th bevel (deg.) | |
| Example | 10.5 | 18.1 | 18.2 | 11.8 | 111 | | 4.065 |
| Comp. Ex. 1 | 10.0 | 18.3 | 18.3 | | 108 | | 3.899 |
| Comp. Ex. 2 | 10.5 | 18.2 | 18.3 | 14.8 | 110 | 145 | 3.521 |

TABLE 2

(Unit: mm)

| Section | 1st bevel L − (L1 + L3) | 2nd and 3rd bevels L1 − L1 | | | | | 4th bevel Height | |
|---|---|---|---|---|---|---|---|---|
| | | L1 | L4 | L4 | L2 | L3 | h1 | h2 |
| Example | 1.530 | 1.564 | 1.411 | 0.513 | 1.358 | 0.971 | 0.065 | 0.376 |
| Comp. Ex. 1 | 2.100 | 1.799 | 1.489 | 0.310 | 0.397 | | 0.125 | 0.450 |
| Comp. Ex. 2 | 1.069 | 1.777 | 1.450 | 0.327 | 0.224 | 0.675 | 0.137 | 0.655 |

The invention claimed is:

1. A medical hollow needle including a needle tube in a cylindrical shape with a blade surface inclined against a central axis thereof at a tip of the needle tube, wherein
the blade surface comprises:
a first inclined surface located on a base end side;
a second inclined surface and a third inclined surface, the second inclined surface and the third inclined surface being located on a tip end side and provided with a same rotational angle in a direction opposite to each other around the central axis relative to the first inclined surface, the second inclined surface and the third inclined surface having a same inclination angle to the central axis, the same inclination angle being larger than the inclination angle of the first inclined surface; and fourth inclined surfaces, at least one of the fourth inclined surfaces being located between the first inclined surface and the second inclined surface, and at least another of the fourth inclined surfaces being located between the first inclined surface and the third inclined surface, the fourth inclined surfaces having rotational angles around the central axis that are the same as the rotational angle of the first inclined surface, the fourth inclined surfaces having inclination angles to the central axis larger than the inclination angle of the first inclined surface and smaller than the inclination angle of the second inclined surface and the third inclined surface, respectively.

2. The medical hollow needle according to claim 1, wherein the inclination angle of the first inclined surface relative to the central axis is set at 10±2 degrees, the inclination angles of the second and third inclined surfaces relative to the central axis are both set at 18±2 degrees, and the inclination angles of each of the fourth inclined surfaces relative to the central axis is set at 12±2 degrees.

3. The medical hollow needle according to claim 1, wherein the fourth inclined surfaces each have a first end on a side of the first inclined surface, the first end being located on the base end side from a center in a central axis direction of the blade surface, and a second end on a side of the second inclined surface and third inclined surface, respectively, the second end being located on the tip end side from the center in the central axis direction of the blade surface.

4. The medical hollow needle according to claim 1, wherein ends of the second inclined surface and the third inclined surface on the base end side are located at 1/4 to 3/4 of a length from the tip end to the base end of the blade surface in the central axis direction.

5. The medical hollow needle according to claim 1, wherein the blade surface further comprises a fifth inclined surface that is provided at a ridge created by the second inclined surface and the third inclined surface at the tip end of the blade surface with the rotational angle set at the same as that of the rotational angle of the first inclined surface around the central axis.

6. The medical hollow needle according to claim 5, wherein the fifth inclined surface is provided as an extension of the fourth inclined surfaces.

7. A method of producing a medical hollow needle that forms a blade surface inclined against a central axis of a needle tube by means of processing a tip of the needle tube of a cylindrical shape with a grinding tool, the method comprising:

a step of forming a first inclined surface located on a base end side of the blade surface by grinding with a first processing surface inclined against the central axis;

a step of forming a second inclined surface located on one side in a circumferential direction at a tip end side of the blade surface by grinding with a second processing surface having an inclination angle larger than the inclination angle of the first inclined surface relative to the central axis by means of differentiating a relative position between the needle tube and the grinding tool by a given rotational angle in one direction around the central axis in reference to the relative position between the grinding tool that grinds the first inclined surface and the needle tube;

a step of forming a third inclined surface located on another side in the circumferential direction at the tip end side of the blade surface by grinding with a third processing surface having a same inclination angle as the inclination angle of the second inclined surface against the central axis by means of differentiating the relative position between the needle tube and the grinding tool by a same rotational angle as the rotational angle of the second inclined surface in an opposite direction thereof around the central axis in reference to the relative position between the grinding tool that grinds the first inclined surface and the needle tube; and a step of forming fourth inclined surfaces with a same rotational angle as the rotational angle of the first inclined surface, at least one of the fourth inclined surfaces being located between the first inclined surface and the second inclined surface, and at least another of the fourth inclined surfaces being located between the first inclined surface and the third inclined surface by grinding with a fourth processing surface having an inclination angle larger than the inclination angle of the first inclined surface but smaller than the inclination angle of the second inclined surface and the third inclined surface, respectively, against the central axis at the relative position between the grinding tool that grinds the first inclined surface and the needle tube.

8. The method of producing a medical hollow needle according to claim 7, wherein the fourth inclined surfaces are formed after forming each of the first inclined surface, the second inclined surface and the third inclined surface.

\* \* \* \* \*